United States Patent
Reddy et al.

(10) Patent No.: US 11,053,211 B2
(45) Date of Patent: Jul. 6, 2021

(54) PROCESS FOR POMALIDOMIDE

(71) Applicant: HETERO RESEARCH FOUNDATION, Hyderabad (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Matta Ramakrishna Krishna Reddy, Hyderabad (IN); Bandi Vamsi Krishna, Hyderabad (IN)

(73) Assignee: HETERO RESEARCH FOUNDATION, Hyderabad (IN)

( * ) Notice: Subject to any disclaimer, the term of this patent is extended or adjusted under 35 U.S.C. 154(b) by 0 days.

(21) Appl. No.: 14/872,743

(22) Filed: Oct. 1, 2015

(65) Prior Publication Data

US 2017/0088537 A1 Mar. 30, 2017

Related U.S. Application Data

(63) Continuation of application No. PCT/IN2014/000205, filed on Apr. 1, 2014.

(30) Foreign Application Priority Data

Apr. 1, 2013 (IN) .......................... 1484/CHE/2013

(51) Int. Cl.
*C07D 401/04* (2006.01)
(52) U.S. Cl.
CPC ........ *C07D 401/04* (2013.01); *C07B 2200/13* (2013.01)
(58) Field of Classification Search
CPC .................................................. C07D 401/04
See application file for complete search history.

(56) References Cited

U.S. PATENT DOCUMENTS

| | | | | |
|---|---|---|---|---|
| 7,994,327 | B2 * | 8/2011 | Ge | ...................... C07D 401/04 546/201 |
| 10,093,647 | B1 | 10/2018 | Atwood | |
| 10,093,648 | B1 | 10/2018 | Atwood | |
| 10,093,649 | B1 | 10/2018 | Atwood | |
| 2003/0152500 | A1 * | 8/2003 | Dalziel | ...................... A23J 3/16 422/245.1 |

FOREIGN PATENT DOCUMENTS

| | | | | |
|---|---|---|---|---|
| CN | 103275062 | * | 9/2013 | |
| CN | 103288797 | A | 9/2013 | |
| CN | 103275062 | A | 4/2016 | |
| WO | 2006024024 | A2 | 3/2006 | |
| WO | WO 2011050962 | A1 * | 5/2011 | ........... C07D 401/04 |
| WO | WO 2013/126326 | | 8/2013 | |
| WO | WO-2013123326 | A1 * | 8/2013 | ................ C12P 1/04 |
| WO | 2017121530 | A1 | 7/2017 | |

OTHER PUBLICATIONS

Gattermann, Ludwig The Practical Methods of Organic Chemistry 1896, Macmillan: London, pp. 1-14.*
Zubrick, James W. The Organic Chem Lab Survival Manual: A Student's Guide to Techniques 4th Ed. 1997, Wiley: New York, pp. 121-125.*
Christian Reichardt "Solvents and Solvent Effects in Organic Chemistry" 2003 WILEY-VCH, Weinheim, pp. 82-83.*
Prescribing Information of Pomalyst Celgene Corporation, Feb. 2013 Update.*
Online "http://web.archive.org/web/20130324144550/http://www.selleckchem.com/products/Pomalidomide(CC-4047).html" accessed Jan. 27, 2017 dated Mar. 24, 2013.*
Online "http://www.accessdata.fda.gov/drugsatfda_docs/nda/2013/204026Orig1s000PharmR.pdf" dated to Dec. 13, 2012 by Google, accessed Oct. 29, 2016.*
Kumar, European Journal of Cancer 2006, 1612-1622.*
Faisal "Reaction Kinetics and Pathway of Hydrothermal Decomposition of Aspartic Acid" International Journal of Chemical Kinetics 2006, pp. 175-180.*
De Haan Industrial Separation Processes, Fundamentals 2013, de Gruyter: Berlin Boston, p. 209.*
Mike McGregor Lecture Notes University of Rhode Island, "Using Melting Point to Determine Purity of Crystalline Solid" Online: "https://www.chm.uri.edu/mmcgregor/chm228/use_of_melting_point_apparatus.pdf" dated May 18, 2009, accessed Aug. 31, 2020.*
Lonare et al., International Journal of Chemical Engineering and Applications, vol. 4, No. 5, Oct. 2013.
Doyen et al., Pomalidomide: a new hope for relapsed and refractory multiple myeloma, Belg J.Hematol 2014;5(4) 137-42.
European Medicines Agency, Assessment Report, Pomalidomide Celene, May 2013.
Revlimid Label, Celegene Corporation, Nov. 2013.
Clark, J., The Effect of Temperature on Reaction Rates, 2002 https://www.chemguide.co.uk/physical/basicrates/temperature.html.
Erik Keller et al. Catalytic enantioselective Michael addition reactions of α-nitroesters to α,β-unsaturated ketones. Tetrahedron: Asymmetry. vol. 8, Issue 20, Oct. 23, 1997, pp. 3403-3413.
Xu et al. Effect of Temperature on the Enantioselectivity in the Oxazaborolidine-Catalyzed Asymmetric Reduction of Ketones. Noncatalytic Borane Reduction, a Nonneglectable Factor in the Reduction System. J. Org. Chem. 2003, 68, 10146-10151 at 10147.
Nicole Stieger and Wilna Liebenberg (Sep. 19, 2012). Recrystallization of Active Pharmaceutical Ingredients, Crystallization, Marcello Rubens Barsi Andreeta, IntechOpen, DOI: 10.5772/52725. Available from: https://www.intechopen.com/books/crystallization-science-and-technology/recrystallization-of-active-pharmaceutical-ingredients.
Banga S, Chawla G, Bansal AK. New trends in crystallization of active pharmaceutical ingredients. Business Briefing: Pharmagenerics 2004, Nov. 1-5.
Davidovich, M. et al., Detection of Polymorphism by Powder X-Ray Diffraction: Interference by preferred orientation. American Pharmaceutical Review, Indianapolis, Indiana, Russell Pub., 2004 7(1), pp. 10, 12, 14, 16 and 100.

(Continued)

Primary Examiner — David K O'Dell
(74) Attorney, Agent, or Firm — Caesar Rivise, PC

(57) ABSTRACT

The present invention provides a novel process for the preparation of pomalidomide crystalline Form I. The present invention also provides a process for the purification of pomalidomide.

3 Claims, 1 Drawing Sheet

(56) References Cited

OTHER PUBLICATIONS

Dimethyl sulfoxide (DMSO). Sigma-Aldrich [online]. [retrieved May 20, 2020]. Retrieved from internet: https://www.sigmaaldrich.com/catalog/product/sial/276855?lang=en&region=US.
N,N-Dimethylformamid. Sigma-Aldrich [online]. [retrieved May 20, 2020]. Retrieved from internet: https://www.sigmaaldrich.com/catalog/product/sial/227056?lang=en&region=US.
N,N-Dimethylacetamide. Sigma-Aldrich [online]. [retrieved May 20, 2020]. Retrieved from internet:https://www.sigmaaldrich.com/catalog/product/sial/271012?lang=en&region=US.
N-Methyl-2-pyrrolidone (NMP, 1-Methyl-2-pyrrolidone). Sigma-Aldrich [online]. [retrieved May 20, 2020]. Retrieved from internet: https://www.sigmaaldrich.com/catalog/product/sial/328634?lang=en&region=US.
Shekunov, et al., Effect of Temperature on crystal growth and crystal properties of paracetamol, J Chem. Soc., Faraday Trans., 1996, 92(3), 439-444.
Gao, et al., Recent Developments in the Crystallization Process: Toward the Pharmaceutical Industry, Engineering 3 (217) 343-353.
Bari et al. (Bari et al. Impurity profile: Significance in Active Pharmaceutical Ingredient. Eurasian Journal of Analytical Chemistry. vol. 2, No. 1, pp. 32-53, 2007.
Rahman, N, et al. The importance of impurity analysis in pharmaceutical products: An integrated approach. Accreditation and Quality Assurance 11(1):69-74 • Apr. 2006.
Misra, B., et al. Pharmaceutical Impurities: A Review. International Journal of Pharmaceutical Chemistry. (2015) 05 (07) 232-239.

\* cited by examiner

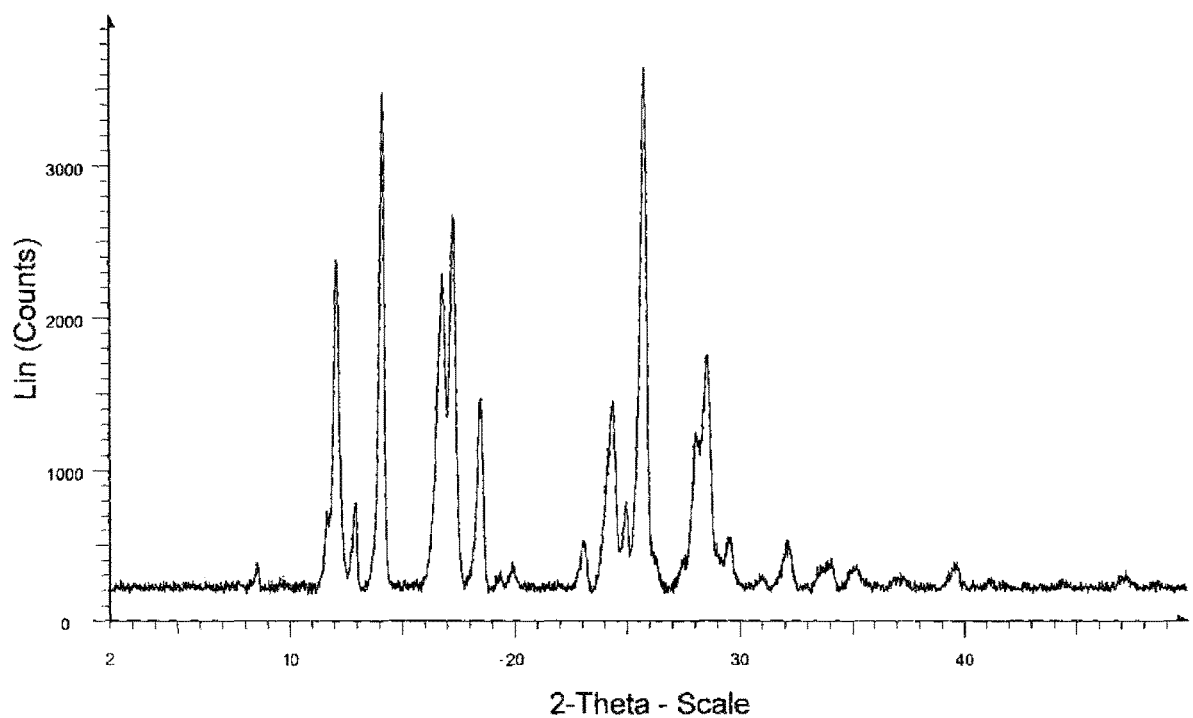

PROCESS FOR POMALIDOMIDE

This application claims the benefit of Indian patent Application No. 1484/CHE/2013, filed on Apr. 1, 2013, which is incorporated herein by reference.

FIELD OF THE INVENTION

The present invention provides a novel process for the preparation of pomalidomide crystalline Form I. The present invention also provides a process for the purification of pomalidomide.

BACKGROUND OF THE INVENTION

Pomalidomide is chemically, 4-Amino-2-(2,6-dioxopiperidin-3-yl)isoindole-1,3-dione and has the structural formula:

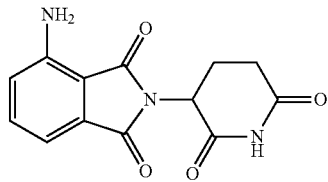 [SMILES: Nc1cccc2c1C(=O)N(C1CCC(=O)NC1=O)C2=O]

Pomalidomide is a derivative of thalidomide that is anti-angiogenic and also acts as an immunomodulator. Pomalidomide is marketed under the brand name Pomalyst® by CELGENE.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning Calorimetry (DSC) and Infrared spectrometry (IR).

Solvent medium and mode of crystallization play very important role in obtaining a crystalline form over the other.

Pomalidomide can exist in different polymorphic forms, which may differ from each other in terms of stability, physical properties, spectral data and methods of preparation.

Pomalidomide and its process were disclosed in U.S. Pat. No. 5,635,517. According to the publication, crystalline solid of pomalidomide was obtained by reducing the 1,3-dioxo-2(2,6-dioxopiperidin-3-yl)-5-nitroisoindoline with palladium carbon in the presence of 1,4-dioxane, filtered and then concentrated to obtain a residual solid. The residual solid was recrystallized with 1,4-dioxane and ethyl acetate to obtain crystalline pomalidomide. The crystalline pomalidomide obtained by the process of the prior art is herein after designated as pomalidomide crystalline Form I. The powdered x-ray diffractogram (PXRD) of pomalidomide crystalline Form I is shown in FIG. 1. Crystalline Form I is characterized by peaks in the powder x-ray diffraction spectrum having 2θ angle positions at about 12.1, 14.1, 16.8, 17.2, 18.5, 24.4, 25.8, 28.1 and 28.6±0.2 degrees.

We have found a novel process for the preparation of consistently reproducible pomalidomide crystalline Form I.

We have also found a novel process for the purification of pomalidomide. The present invention is intended to enhance the purity of pomalidomide without much loss in the yield. The process of the invention may be used for obtaining pomalidomide in high purity with less than 0.1% of any individual impurities.

Thus, one object of the present invention is to provide a novel process for the preparation of consistently reproducible pomalidomide crystalline Form I.

Another object of the present invention is to provide a novel process for the purification of pomalidomide.

SUMMARY OF THE INVENTION

In one aspect, the present invention provided a process for the preparation of pomalidomide crystalline Form I, which comprises:
  a) suspending pomalidomide in dimethylformamide, dimethylacetamide or dimethyl sulfoxide;
  b) heating the suspension obtained in step (a) above 70° C.;
  c) adding anti-solvent to the solution obtained in step (b); and
  d) isolating pomalidomide crystalline Form I.

In another aspect, the present invention provided a process for the purification of pomalidomide, which comprises:
  a) suspending pomalidomide in an organic solvent;
  b) heating the suspension obtained in step (a) at reflux;
  c) treating the solution obtained in step (b) with carbon;
  d) cooling the solution;
  e) optionally adding an alcoholic solvent, water or an acetic acid; and
  f) isolating the pure pomalidomide.

BRIEF DESCRIPTION OF THE DRAWING

FIG. 1 is X-ray powder diffraction spectrum of pomalidomide crystalline Form I.

Powder X-ray diffraction spectrum was measured on a bruker AXS D8 advance powder X-ray diffractometer having a copper-Kα radiation. Approximately 500 mg of sample was gently flattered on a sample holder and scanned from 2 to 50 degrees two-theta, at 0.020 degrees two theta per step and a step time of 1 second. The sample was simply placed on the sample holder. The sample was rotated at 30 rpm at a voltage 40 kV and current 35 mA.

DETAILED DESCRIPTION OF THE INVENTION

The term "room temperature" refers to temperature at about 25 to 35° C.

According to one aspect of the present invention, there is provided a process for the preparation of pomalidomide crystalline Form I, which comprises:
  a) suspending pomalidomide in dimethylformamide, dimethylacetamide or dimethyl sulfoxide;

b) heating the suspension obtained in step (a) above 70° C.;
c) adding anti-solvent to the solution obtained in step (b); and
d) isolating pomalidomide crystalline Form I.

The reaction in step (b) may preferably be heated to 80 to 110° C.

The anti-solvent used in step (c) may preferably be a solvent or a mixture of solvent selected from cyclohexane, hexane, n-heptane, benzene, toluene, xylene, tetrahydrofuran, methyl tert-butyl ether and diethyl ether. More preferably the anti-solvents are toluene and methyl tert-butyl ether.

Pomalidomide crystalline Form I may be isolated in step (d) by the methods known such as filtration or centrifugation.

According to another aspect of the present invention, there is provided a process for the purification of pomalidomide, which comprises:
a) suspending pomalidomide in an organic solvent;
b) heating the suspension obtained in step (a) at reflux;
c) treating the solution obtained in step (b) with carbon;
d) cooling the solution;
e) optionally adding an alcoholic solvent, water or an acetic acid; and
f) isolating the pure pomalidomide.

The term "pure pomalidomide" refers to pomalidomide having the purity greater than about 98.5% by weight, preferably greater than about 99% by weight, and more preferably greater than about 99.5% by weight.

The organic solvent used in step (a) may preferably be a solvent or a mixture of solvents selected from ethyl acetate, methyl acetate, methylene chloride, ethylene chloride, dimethylformamide, dimethylacetamide, dimethyl sulfoxide and N-methylpyrrolidone, and more preferably the organic solvents are dimethylformamide, dimethylacetamide, dimethyl sulfoxide and N-methylpyrrolidone.

The step (d) may conveniently be carried out at room temperature.

The alcoholic solvent used in step (a) may preferably be a solvent or a mixture of solvents selected from methanol, ethanol, propanol, isopropyl alcohol and n-butanol, and more preferably the alcoholic solvent is n-butanol.

Isolation of pure pomalidomide in step (f) can be performed by conventional methods such as cooling, removal of solvents, concentrating the reaction mass, adding an anti-solvent, extraction with a solvent and the like.

The contents of pomalidomide and the impurities are determined by High performance liquid chromatography (HPLC).

The invention will now be further described by the following examples, which are illustrative rather than limiting.

EXAMPLES

Example 1

Preparation of Pomalidomide

Dimethylformamide (1500 ml) was added to 3-(4-nitro-1-oxoisoindolin-2-yl)piperidine-2,6-dione (150 gm) and then stirred for 30 minutes at room temperature to obtain a clear solution. To the solution was added 10% palladium carbon and then applied 4 Kg of hydrogen pressure at room temperature. The reaction mass was stirred for 3 hours at room temperature and temperature of the reaction mass was raised to 60 to 65° C. The reaction mass was filtered through hi-flow bed and then concentrated to obtain a residual solid. To the residual solid was added ethyl acetate (600 ml) and then heated to reflux. The reaction mass was maintained for 30 minutes at reflux and then cooled to room temperature. The contents were stirred for 1 hour at room temperature and filtered. The solid obtained was then dried to obtain 136 gm of pomalidomide.
Chromatographic purity: 97.5%.

Example 2

Preparation of Pomalidomide Crystalline Form I

Pomalidomide (2.5 gm) as obtained in example 1 was suspended in dimethylformamide (25 ml) and then heated to 90° C. to obtain a clear solution. To the solution was added toluene (25 ml) and stirred for 3 hours at room temperature. The separated solid was filtered and then dried to obtain 2 gm of pomalidomide crystalline Form I.
Chromatographic purity: 99.5%.

Example 3

Preparation of Pomalidomide Crystalline Form I

Pomalidomide (2.5 gm) was suspended in dimethylformamide (25 ml) and then heated to 90° C. to obtain a clear solution. To the solution was added methyl tert-butyl ether (25 ml) and stirred for 3 hours at room temperature. The separated solid was filtered and then dried to obtain 2 gm of pomalidomide crystalline Form I.
Chromatographic purity: 99.45%.

Example 4

Purification of Pomalidomide

Pomalidomide (30 gm; HPLC Purity: 97.5%) as obtained in example 1 was suspended in dimethylacetamide (120 ml) and then heated to reflux to obtain a clear solution. The solution was subjected to carbon treatment at reflux and then cooled to room temperature. The contents were stirred for 2 hours at room temperature and filtered. The solid obtained was dried to obtain 20 gm of pure pomalidomide.
Chromatographic purity: 99.89%.

Example 5

Purification of Pomalidomide

Pomalidomide (30 gm) was suspended in dimethyl sulfoxide (90 ml) and then heated to reflux to obtain a clear solution. The solution was subjected to carbon treatment at reflux and then cooled to room temperature. The contents were stirred for 2 hours at room temperature and filtered. The solid obtained was dried to obtain 19 gm of pure pomalidomide.
Chromatographic purity: 99.86%.

Example 6

Purification of Pomalidomide

Pomalidomide (30 gm) was suspended in dimethylformamide (300 ml) and then heated to reflux to obtain a clear solution. The solution was subjected to carbon treatment at reflux and then cooled to room temperature. The contents were stirred for 2 hours at room temperature and filtered. The solid obtained was dried to obtain 18 gm of pure pomalidomide.
Chromatographic purity: 99.87%.

Example 7

Purification of Pomalidomide

Pomalidomide (30 gm) was suspended in N-methylpyrrolidone (240 ml) and then heated to reflux to obtain a clear solution. The solution was subjected to carbon treatment at reflux and then cooled to room temperature. The contents were stirred for 2 hours at room temperature and filtered. The solid obtained was dried to obtain 18.5 gm of pure pomalidomide.
Chromatographic purity: 99.87%.

Example 8

Purification of Pomalidomide

Pomalidomide (30 gm) was suspended in dimethylacetamide (120 ml) and then heated to reflux to obtain a clear solution. The solution was subjected to carbon treatment at reflux and then cooled to room temperature. To the reaction mass was added n-butanol (120 ml) and stirred for 2 hours at room temperature. The separated solid was filtered and then dried to obtain 23 gm of pure pomalidomide.
Chromatographic purity: 99.96%.

Example 9

Purification of Pomalidomide

Pomalidomide (10 gm) was suspended in dimethyl sulfoxide (30 ml) and then heated to reflux to obtain a clear solution. The solution was subjected to carbon treatment at reflux and then cooled to room temperature. To the reaction mass was added n-butanol (40 ml) and stirred for 2 hours at room temperature. The separated solid was filtered and then dried to obtain 7 gm of pure pomalidomide.
Chromatographic purity: 99.91%.

Example 10

Purification of Pomalidomide

Pomalidomide (10 gm) was suspended in dimethylformamide (100 ml) and then heated to reflux to obtain a clear solution. The solution was subjected to carbon treatment at reflux and then cooled to room temperature. To the reaction mass was added n-butanol (40 ml) and stirred for 2 hours at room temperature. The separated solid was filtered and then dried to obtain 7 gm of pure pomalidomide.
Chromatographic purity: 99.93%.

Example 11

Purification of Pomalidomide

Pomalidomide (15 gm) was suspended in N-methylpyrrolidone (120 ml) and then heated to reflux to obtain a clear solution. The solution was subjected to carbon treatment at reflux and then cooled to room temperature. To the reaction mass was added n-butanol (60 ml) and stirred for 2 hours at room temperature. The separated solid was filtered and then dried to obtain 10 gm of pure pomalidomide.
Chromatographic purity: 99.9%.

Example 12

Purification of Pomalidomide

Pomalidomide (30 gm) was suspended in dimethylacetamide (120 ml) and then heated to reflux to obtain a clear solution. The solution was subjected to carbon treatment at reflux and then cooled to 100° C. To the reaction mass was added water (720 ml) slowly for 45 minutes at 100° C. and then cooled to room temperature. The contents were stirred for 2 hours at room temperature and filtered. The solid obtained was dried to obtain 25 gm of pure pomalidomide.
Chromatographic purity: 99.79%.

Example 13

Purification of Pomalidomide

Example 12 was repeated using dimethyl sulfoxide solvent instead of dimethylacetamide solvent to obtain pure pomalidomide.

Example 14

Purification of Pomalidomide

Example 12 was repeated using dimethylformamide solvent instead of dimethylacetamide solvent to obtain pure pomalidomide.

Example 15

Purification of Pomalidomide

Example 12 was repeated using N-methylpyrrolidone solvent instead of dimethylacetamide solvent to obtain pure pomalidomide.

Example 16

Purification of Pomalidomide

Pomalidomide (30 gm) was suspended in dimethylacetamide (120 ml) and then heated to reflux to obtain a clear solution. The solution was then cooled to 120° C. and then subjected to carbon treatment, filtered. To the filtrate was added acetic acid (120 ml) at 120° C. under stirring and then cooled to room temperature. The contents were stirred for 2 hours at room temperature and filtered. The solid obtained was dried to obtain 25 gm of pure pomalidomide.
Chromatographic purity: 99.91%.

Example 17

Purification of Pomalidomide

Example 16 was repeated using dimethyl sulfoxide solvent instead of dimethylacetamide solvent to obtain pure pomalidomide.

Example 18

Purification of Pomalidomide

Example 16 was repeated using dimethylformamide solvent instead of dimethylacetamide solvent to obtain pure pomalidomide.

Example 19

Purification of Pomalidomide

Example 16 was repeated using N-methylpyrrolidone solvent instead of dimethylacetamide solvent to obtain pure pomalidomide.

We claim:

1. A process for the preparation of pomalidomide crystalline Form I with the XRPD spectrum of FIG. 1, which comprises:

a) suspending pomalidomide in dimethylformamide, dimethylacetamide or dimethyl sulfoxide;

b) heating the suspension obtained in step (a) above 70° C.;

c) adding an anti-solvent selected from the group consisting of cyclohexane, hexane, n-heptane, benzene, toluene, xylene, tetrahydrofuran, methyl tert-butyl ether, diethyl ether, and mixtures thereof to the solution obtained in step (b) at above 70° C.;

d) cooling to room temperature; and e) isolating pomalidomide crystalline Form I with the XRPD spectrum of FIG. 1.

2. The process according to claim 1, wherein the reaction in step (b) is heated to 80 to 110° C.

3. The process as claimed in claim 1, wherein the anti-solvents are toluene and methyl tert-butyl ether.

* * * * *